United States Patent
Epperly et al.

(10) Patent No.: US 10,624,687 B2
(45) Date of Patent: Apr. 21, 2020

(54) SUTURE PASSING APPARATUS AND METHOD OF USING SAME

(71) Applicant: Advanced Orthopaedic Solutions, Inc., Torrance, CA (US)

(72) Inventors: Scott J Epperly, Redondo Beach, CA (US); J. Tracy Watson, Town and Country, MO (US); Mark A Steinhauer, Redondo Beach, CA (US)

(73) Assignee: Advanced Orthopaedic Solutions, Inc., Torrance, CA (US)

( * ) Notice: Subject to any disclaimer, the term of this patent is extended or adjusted under 35 U.S.C. 154(b) by 184 days.

(21) Appl. No.: 15/058,130

(22) Filed: Mar. 1, 2016

(65) Prior Publication Data

US 2017/0252078 A1    Sep. 7, 2017

(51) Int. Cl.
*A61B 17/80* (2006.01)
*A61B 17/04* (2006.01)
*A61B 17/00* (2006.01)

(52) U.S. Cl.
CPC ........ *A61B 17/808* (2013.01); *A61B 17/0469* (2013.01); *A61B 17/0482* (2013.01); *A61B 17/0483* (2013.01); *A61B 17/0485* (2013.01); *A61B 2017/00349* (2013.01)

(58) Field of Classification Search
CPC .................................................. A61B 17/0483
See application file for complete search history.

(56) References Cited

U.S. PATENT DOCUMENTS

| | | | |
|---|---|---|---|
| 6,152,934 A * | 11/2000 | Harper | A61B 17/04 606/139 |
| 8,888,795 B2 | 11/2014 | Chu | |
| 9,011,466 B2 | 4/2015 | Adams et al. | |
| 9,089,322 B2 | 7/2015 | Spenciner et al. | |
| 2003/0113906 A1 * | 6/2003 | Sangha | A61B 10/0051 435/287.2 |
| 2015/0024339 A1 | 1/2015 | Calderon | |

* cited by examiner

*Primary Examiner* — Andrew Yang
(74) *Attorney, Agent, or Firm* — Burgess Law Office, PLLC (57) ABSTRACT

A suture passing apparatus including an elongated body having opposite ends. A head is located on one end with a retainer assembly located at the other end. A recess extends from the aperture along the elongated body. A loop of a flexible member is placed in the aperture and over a projection extending into the aperture. The flexible member is placed in the recess extending from the aperture along the elongated body.

19 Claims, 11 Drawing Sheets

SUTURE PASSING APPARATUS AND METHOD OF USING SAME

CROSS-REFERENCE TO RELATED APPLICATIONS

Not Applicable.

BACKGROUND OF THE INVENTION

1. Field of the Invention

The present invention relates generally an apparatus and method for passing a suture; more specifically, passing a suture while creating a passage through soft-tissue.

2. Description of Related Art

During surgery, a surgeon may use a periosteal elevator to reflect the attached periosteum from the underlying bone creating a passageway and corresponding space for a bone plate. The periosteum should be stripped sparingly and only sufficiently for application of the plate. After removing the periosteal elevator, the surgeon pushes the bone plate into and attempts to follow the created passageway to properly position the bone plate.

The surgeon may pass a suture retriever through the created passage created in the soft-tissue. Generally, the suture retriever is forcibly driven through the soft-tissue. The suture is then attached to the suture retriever, wherein the retriever is withdrawn pulling the suture with it.

Each time an instrument, including the bone plate, is driven through the passageway the risk increases of additional damage to the surrounding soft-tissue and stripping additional periosteum from the bone risking damage to the blood supply of the bone.

SUMMARY OF THE INVENTION

A suture passing apparatus including an elongated body having a first end and a second end. A head is located on the first end. A retainer assembly is located at the second end. A recess is located in the elongated body, the recess extending longitudinally from the head to the retainer assembly.

A further exemplary embodiment includes a method of installing a bone plate including providing an instrument having an elongated body including a head portion. The head portion including an aperture and a projection extending into the aperture. A recess extends from the aperture along the elongated body. A loop of a flexible member is placed in the aperture and over the projection. The flexible member is placed in the recess extending from the aperture along the elongated body. The instrument, specifically the head portion, is used to create a passageway adjacent the underlying bone. After creating the passageway, the loop of flexible member is removed from the projection, whereby the flexible member may be secured to a bone plate. The instrument is then removed and the flexible member used to pull the bone plate through the passageway and into position.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

Figure 1:
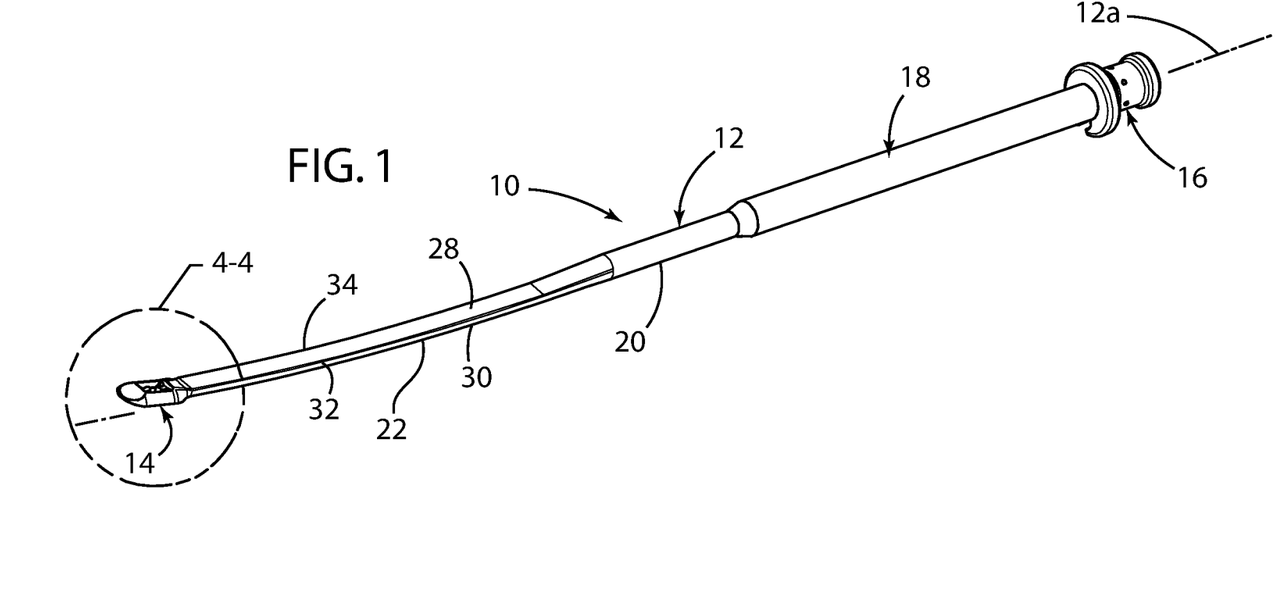
FIG. 1 is a perspective view of a suture passer according to one embodiment of the present invention.
Figure 2:
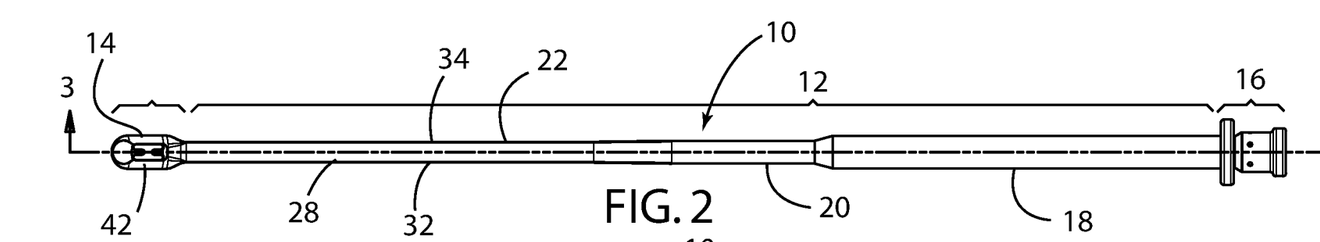
FIG. 2 is a top view of the suture passer of FIG. 1.
Figures 3, 3A:
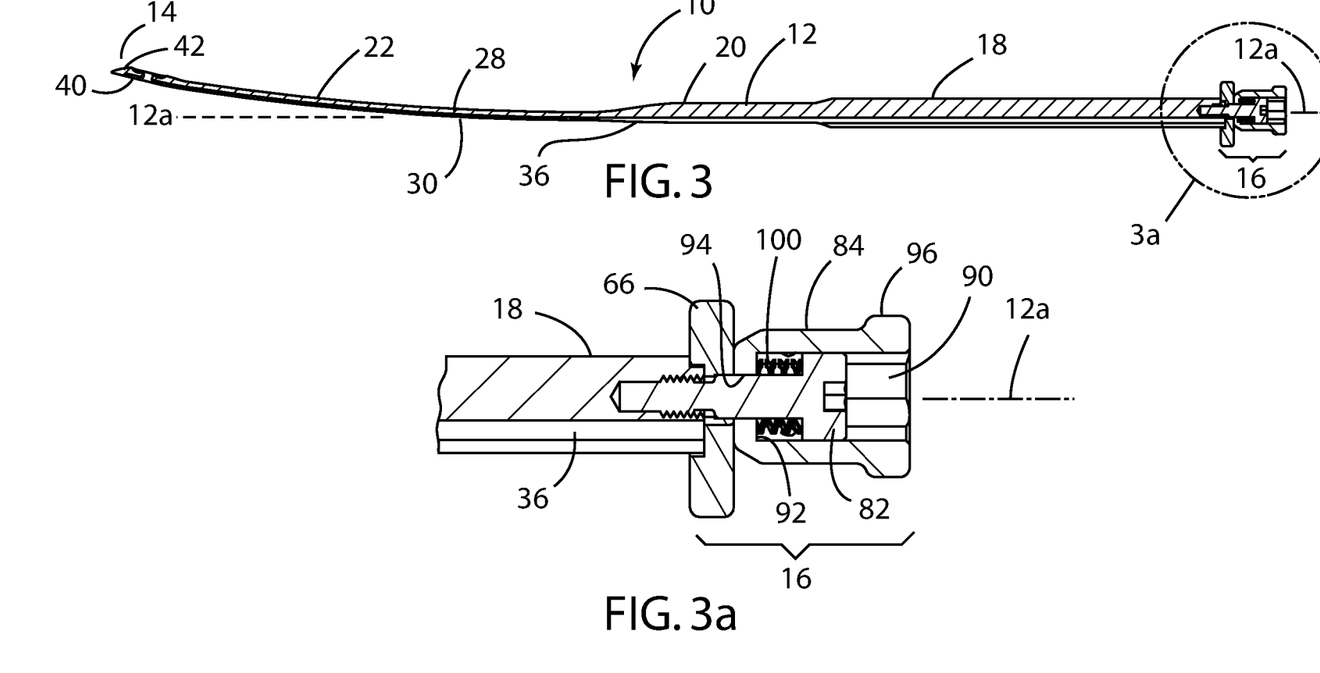
FIG. 3 is a sectional view of the suture passer of FIG. 1 taken along lines 3-3 of FIG. 2.
FIG. 3a is and enlarged view of the retainer assembly taken in the circle 3a-3a of FIG. 3.
Figure 4:
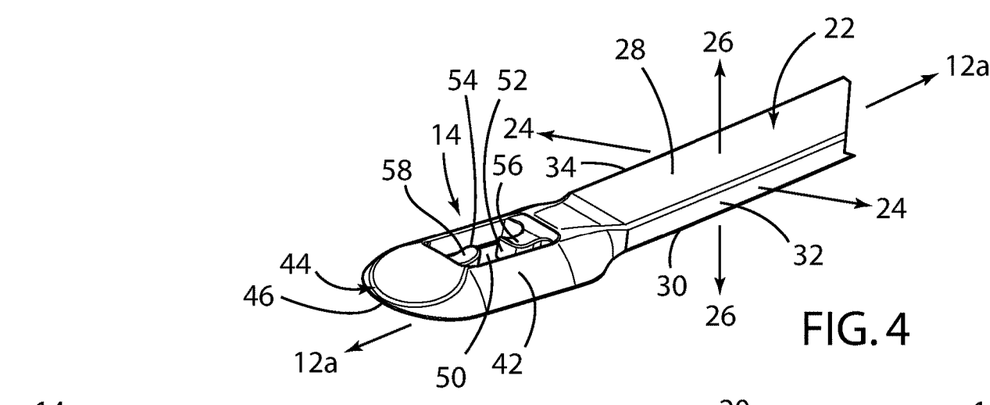
FIG. 4 is an enlarged view of the suture passer of FIG. 1 taken in the circle 4-4 of FIG. 1.
Figure 5:
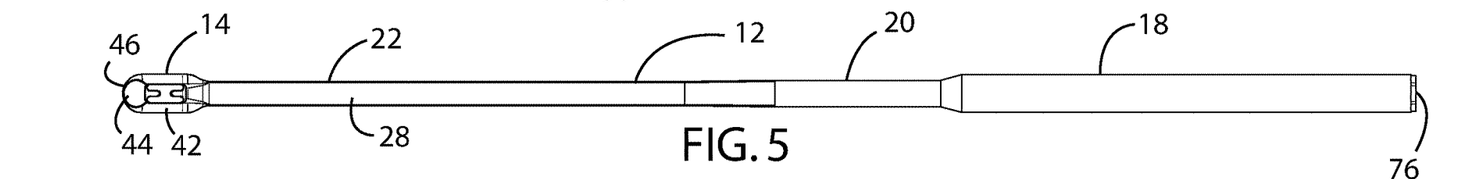
FIG. 5 is a top view of an elongated body of the suture passer of FIG. 1.

FIGS. 1-3 illustrate an exemplary embodiment of the present invention wherein the suture passing apparatus, seen generally at 10, includes an elongated body 12 having a head 14 at one end. A retainer assembly 16 is attached at the other end.

As illustrated in FIG. 1 the elongated body 12 includes a generally cylindrical handle portion 18, a transition portion 20, and a blade portion 22. As illustrated, the blade portion 22 is a broad, flat part with a generally rectangular cross section, having a major axis 24 and a minor axis 26 see FIG. 9. Wherein the major axis 24 extends in the direction of the width of the blade portion 22 and the minor axis 26 extends in the direction of the thickness of the blade portion 22. The major axis 24 is also referred to herein as the lateral axis of the blade portion 22. When referred to, a bending axis is an axis generally perpendicular to the longitudinal axis 12a of the elongated member 12.

Figures 8, 9:
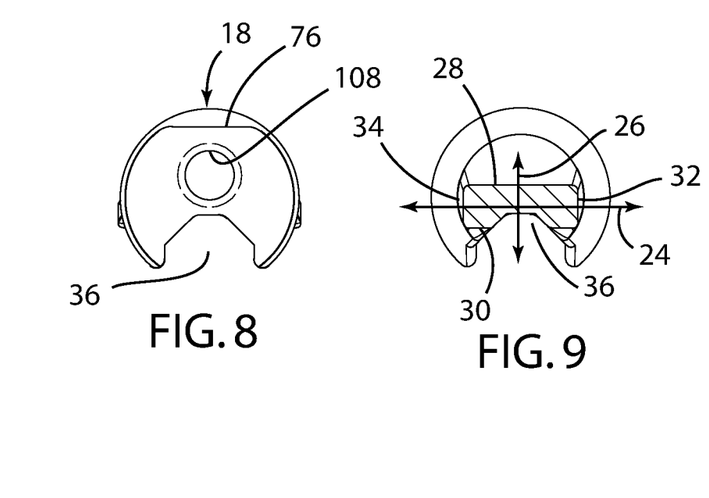
FIG. 8 is an end view of one end of the elongated body of the suture passer of FIG. 1.
FIG. 9 is a sectional view of the elongated body of the suture passer of FIG. 1 taken along lines 9-9 of FIG. 7.

The blade portion 22 has a substantially planar top surface 28, a substantially planar bottom surface 30 and substantially planar, opposed side surfaces 32, 34. In the disclosed example, the distance between the top surface 28 and bottom surface 30, the distance along the minor axis 26, defines the thickness of the blade portion 22. Further, the distance between the opposed side surfaces, 32, 34, the distance along the major axis 24, defines the width of the blade portion 22. As illustrated, the width of the blade portion 22 is greater than its thickness. Accordingly, the blade portion 22 has greater flexibility; i.e., it bends more easily about the major axis 24 and has a greater rigidity or resists bending about the minor axis 26.

Figure 6:
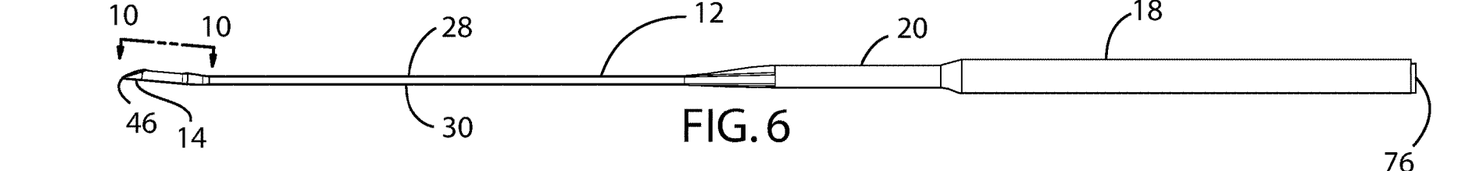
FIG. 6 is a side view of an elongated body of the suture passer of FIG. 1.

FIG. 3 illustrates one example where in the blade portion 22 curves upward; i.e. away from the longitudinal axis 12a in the direction of the minor axis 26. The curvature allowing the operator to start the head portion 14 and bottom surface 40 thereof against a bone while the handle portion 18 is spaced from the bone to increase the angle of entry, more easily follow bone curvature, and provide spacing for the handle portion 18 from adjacent soft tissue. FIG. 6 illustrates another embodiment wherein only the head portion 14 is angled or curved upward.

Figure 7:
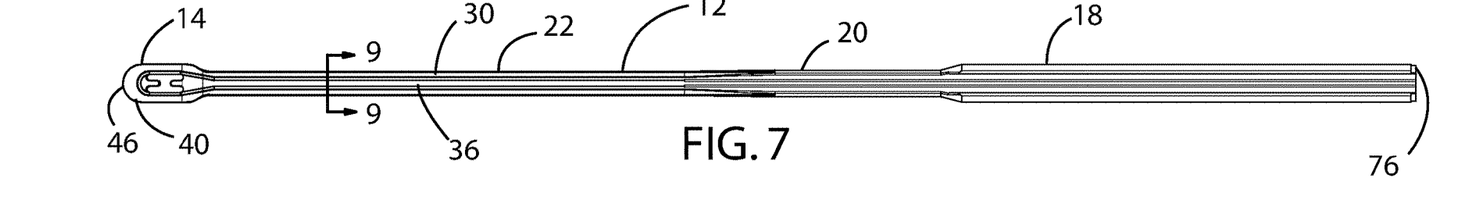
FIG. 7 is a bottom view of an elongated body of the suture passer of FIG. 1.
Figure 11:
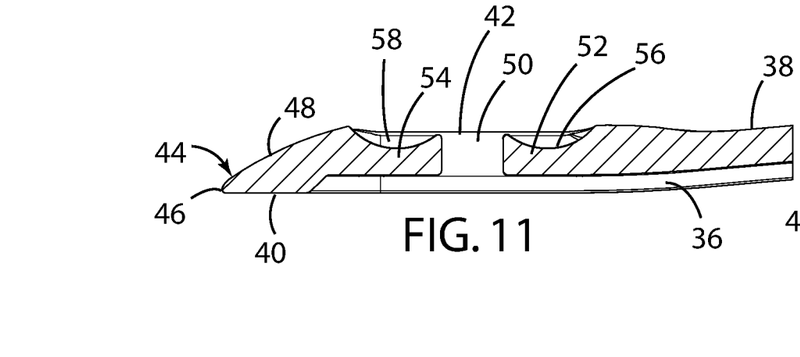
FIG. 11 is a sectional view of the head portion of the suture passer of FIG. 1 taken along lines 11-11 of FIG. 10.
Figure 12:
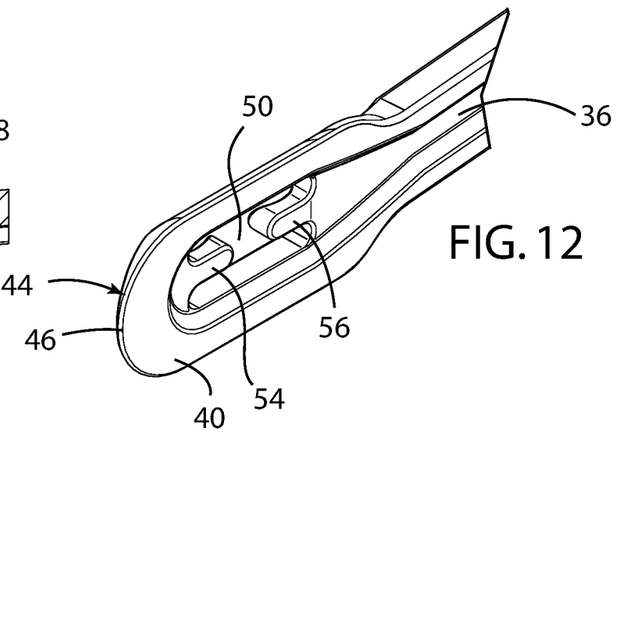
FIG. 12 is a perspective view of the underside or bottom of the head portion of the suture passer of FIG. 1.
Figure 13:
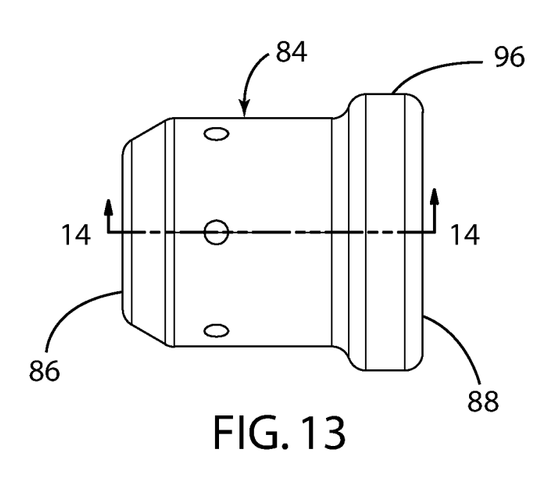
FIG. 13 is a side view of retainer of the suture passer of FIG. 1.
Figure 14:
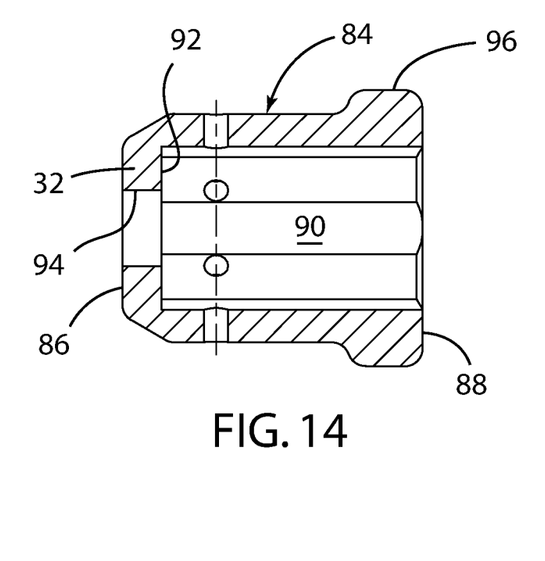
FIG. 14 is a sectional view of the retainer of the suture passer of FIG. 1 taken along lines 14-14 of FIG. 13.
Figure 15:
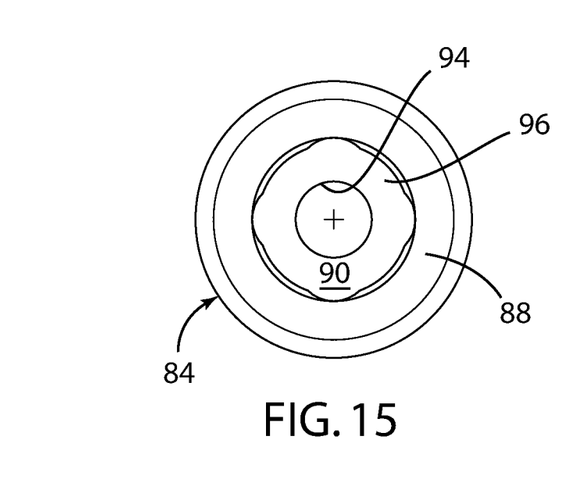
FIG. 15 is an end view of the retainer of the suture passer of FIG. 1 showing the right end of FIG. 13.
Figure 16:
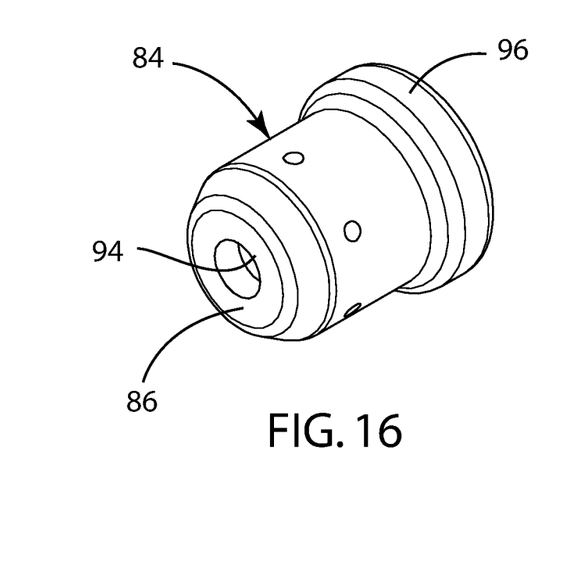
FIG. 16 is a perspective view of the retainer of the suture passer of FIG. 1.
Figure 17:
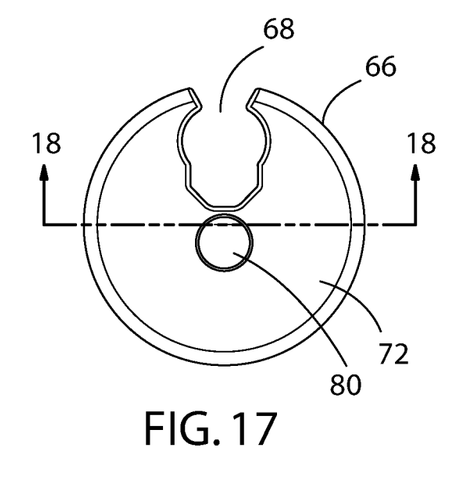
FIG. 17 is a rear view of a flange of the suture passer of FIG. 1.
Figure 18:
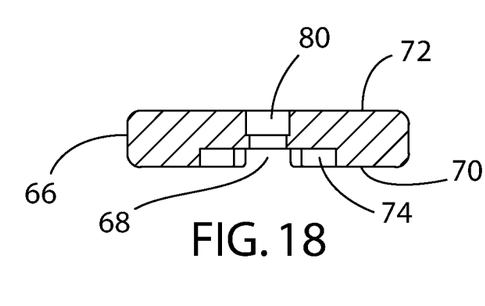
FIG. 18 is a sectional view of the flange of the suture passer of FIG. 1 taken along lines 18-18 of FIG. 17.
Figure 19:
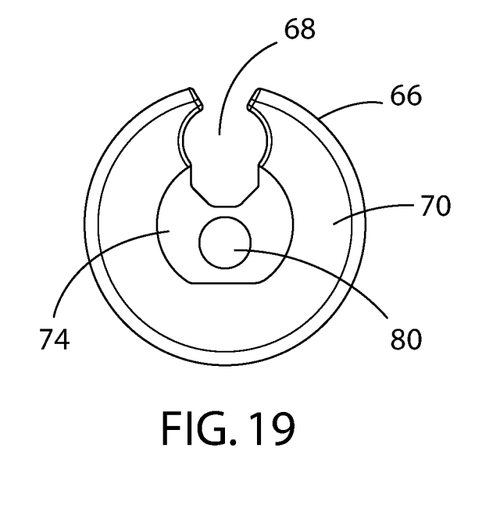
FIG. 19 is a front view of a flange of the suture passer of FIG. 1.
Figure 20:
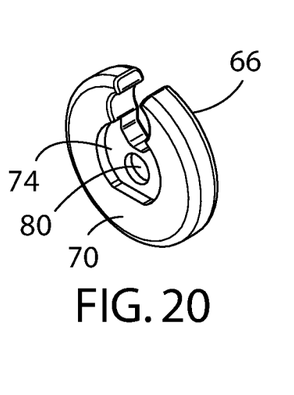
FIG. 20 is a front perspective view of the flange of the suture passer of FIG. 1.
Figure 21:
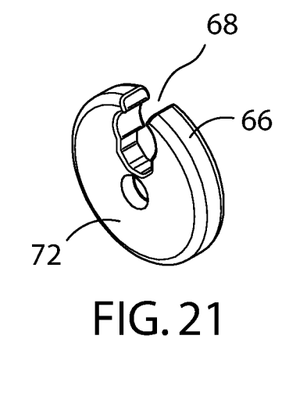
FIG. 21 is a rear perspective view of the flange of the suture passer of FIG. 1.

As illustrated in FIGS. 3 and 7 the elongated body 12 includes a recess 36 extending rearwardly from the head 14, see FIGS. 11-12, to the retainer assembly 16. In the present example, the recess 36 is a longitudinally extending groove; i.e. a narrow channel, formed in the bottom surface 30 of the blade portion 22, extending through the transition portion 20 and handle portion 18, see FIG. 8. As disclosed, the recess extends from the head 14 to the retainer assembly 16. As set forth more fully herein, the recess 36 provides a gap or space for a flexible member or suture 38, see FIGS. 22-23. Placing the recess 36 on the bottom of the elongated body 12 provides two advantages. First, the elongated body 12 typically flexes or bends upward whereby the flexible member or suture 38 remains in the recess 36 and does not bow out. Second, the lower or bottom surface 30 remains adjacent the bone surface, which also helps retain the flexible member or suture 30 in the recess 36.

As illustrated, the head portion 14 has a planar bottom surface 40 and a curved or beveled top surface 42. The head portion 14 includes a tip 44 having a leading edge 46. The leading edge 46, when viewed from the top, is configured in a curved or swept shape. As illustrated in the disclosed embodiment, starting at the bottom surface 40, the tip 44 includes an upwardly sloping or beveled surface 48 forming a chisel. The upwardly sloping or beveled surface 48 operates with the leading edge 46 and curved or beveled top surface 42 to bluntly dissect or reflect the underlying tissue and periosteum from the underlying bone creating a passageway. In the disclosed example, see FIGS. 10-12 the head 14 is slightly larger than the blade portion 22 whereby the blade portion 22 travels through a passageway created by the head 14. It should be understood that while a specific configuration is illustrated in the disclosed example, other configurations suitable for bluntly dissecting or reflecting the underlying tissue and periosteum may also be used.

Figure 10:
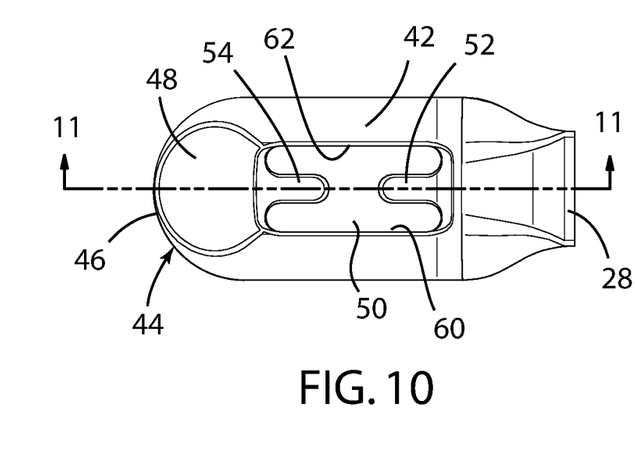
FIG. 10 is an enlarged, top view of a head portion of the suture passer of FIG. 1 viewed in the direction of lines 10-10 of FIG. 6.

The head 14 further includes an aperture 50 shown extending between the top surface 42 and bottom surface 40 of the head 14. The aperture 50 includes two longitudinally extending and opposed projections 52, 54. As illustrated, the opposed projections 52, 54 extend longitudinally, in the direction of the longitudinal axis 12a, into the aperture 50. Each projection 52, 54 includes a concave or curved upper surface 56, 58. The respective surfaces 56, 58 forming a depression or seat for the suture or flexible member 38, keeping the suture or flexible member 38 at or below the upper surface 42 of the head 14.

In the disclosed embodiment, the aperture 50 is an H-shaped aperture; see FIG. 10, wherein the projections 52, 54 extending inwardly are equally spaced from the longitudinal sidewalls 60, 62 of the aperture 50. This is but one example, whereby the respective projections 52, 54 are positioned to engage a loop 64 of the suture or flexible member 38, shown in FIG. 22 engaged to projection 52.

The retainer assembly 16 includes a cylindrical flange 66 having an inwardly extending notch 68. The flange 66 includes a front surface 70 and a rear surface 72, with the front surface 70 being that surface positioned adjacent the handle portion 18 of the elongated body 12. The front face 70 includes a substantially D-shaped cavity or opening 74 extending inwardly from the front face 70 into the flange 66. The D-shaped cavity or opening 74 cooperates with a corresponding D-shaped projection 76 extending rearwardly from the end 78 of the handle portion 18 of the elongated body 12, see FIG. 8. The correspondingly shaped cavity and projection operate to properly orient the notch 68 in the flange 66 whereby it aligns with the recess 36. The flange 66 further includes an aperture 80 extending between the front surface 70 and rear surface 72. The aperture sized for receiving a fastener 82, see FIG. 3, used to secure the flange 66 to the elongated body 12 using a threaded aperture 108 extending inwardly into the end of the handle portion 18 of the elongated body 12.

The retainer assembly 16 further includes a knob 84 shown in FIGS. 13-16. The knob 84 has a generally elongated cylindrical configuration having a front end 86 and a rear end 88 with the front end 86 being that end closest to the flange 66 when positioned adjacent the flange 66. A socket or blind bore 90 extends inwardly from the rear end 88 toward the front end 86 and terminates at a front wall 92. An aperture 94 extends through the front wall 92. The aperture 94 sized for receiving the fastener 82, see FIG. 3. The knob 84 includes a rim or lip 96 extending radially outward and circumferentially about the outer surface 98 of the knob 84. The rim or lip 96 provides a grasping surface whereby a user may grasp and pull the knob 84.

As illustrated in FIG. 3a the fastener 82 slidably secures the knob 84 to the handle portion 18 of the elongated body 12. A spring 100 disposed between the head 102 of the fastener 82 and the front wall 92 of the knob 84 biases the knob 84 forward, toward the flange 66.

Figure 22:
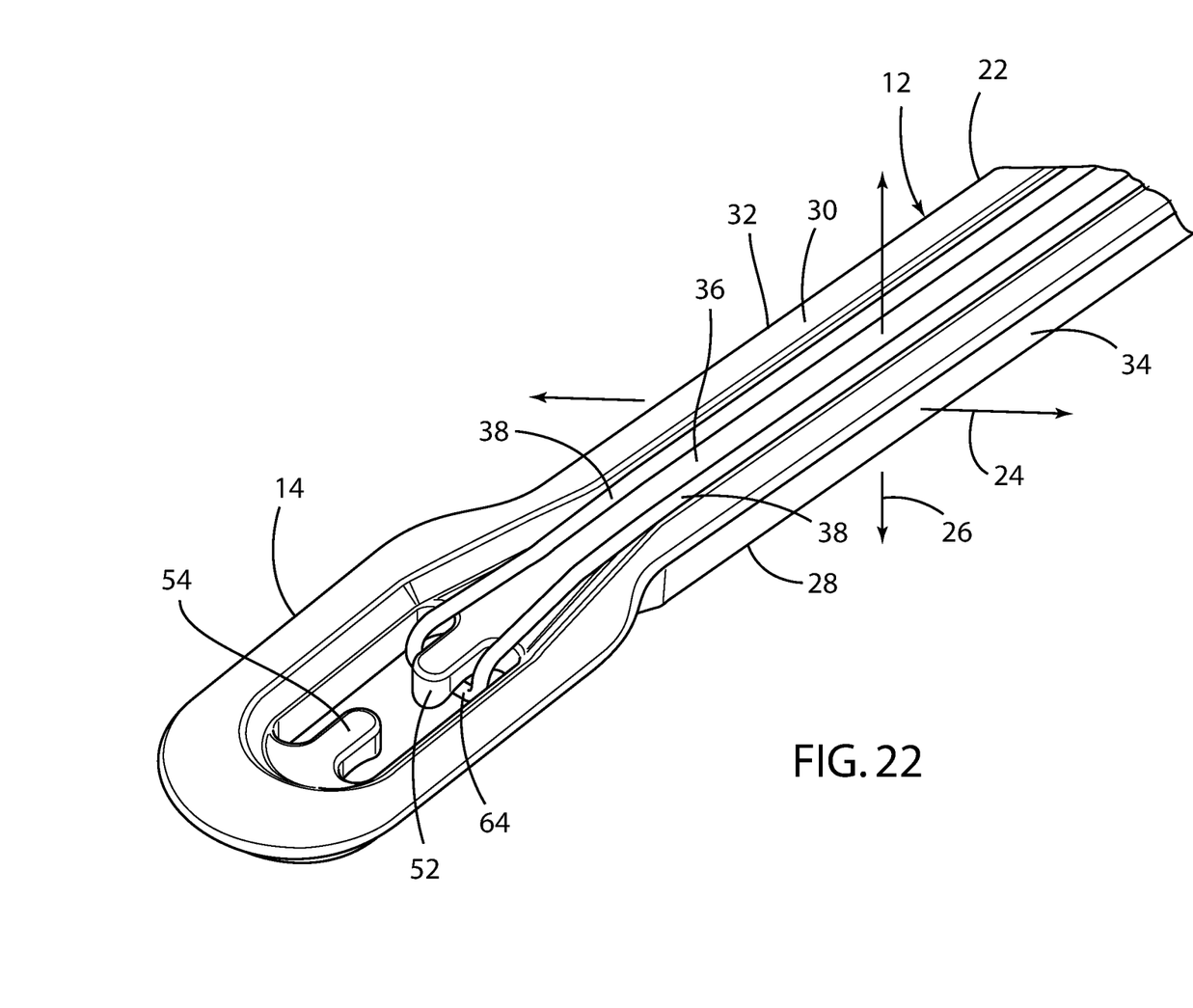
FIG. 22 is a bottom perspective view of a portion of the suture passer of FIG. 1 illustrating a suture held thereon.
Figure 23:
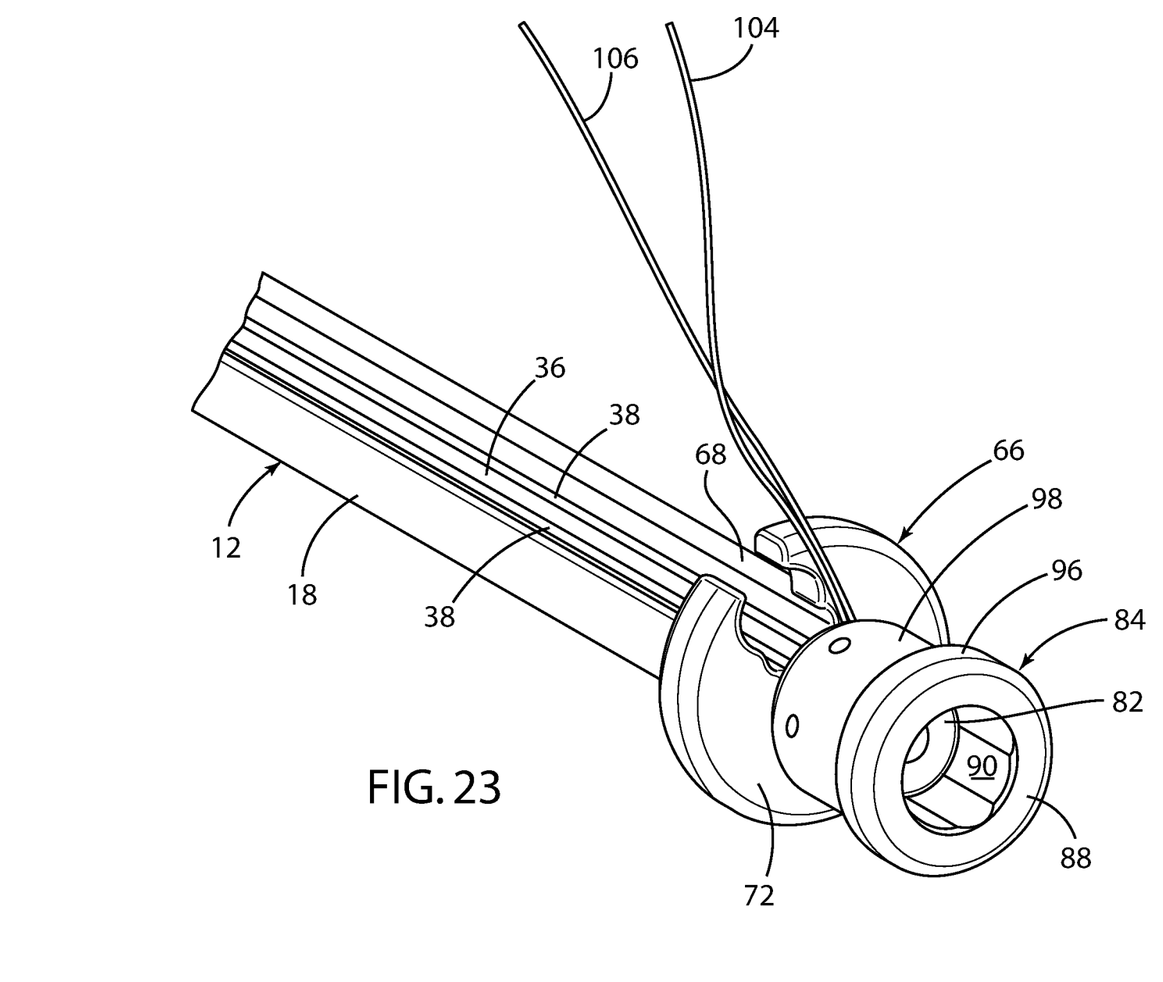
FIG. 23 is a rear perspective view the flange and knob of the suture passer of FIG. 1 illustrating the suture secured to the suture passer.

FIGS. 22-23 illustrate the suture or flexible member 38 installed or in place on the suture passer 10. As illustrated, the loop 64 of the suture or flexible member 38 is placed over the projection 52 and received in the curved surface 56 of the projection 52. The suture or flexible member 38 extends rearwardly from the head 14 to the retainer assembly 16 in the recess 36. The ends 104, 106 of the suture or flexible member 38, and correspondingly the suture or flexible member 38, pass through the notch 68 in the flange 66. As illustrated the ends 104, 106 of the suture or flexible member 38 wrap around the fastener 82 and are sandwiched between the knob 84 and cylindrical flange 66 and held in place by the compressive force exerted by spring 100. In this manner, suture passer 10 captures and secures the suture or flexible member 38 in place on the suture passer 10.

Figure 24:
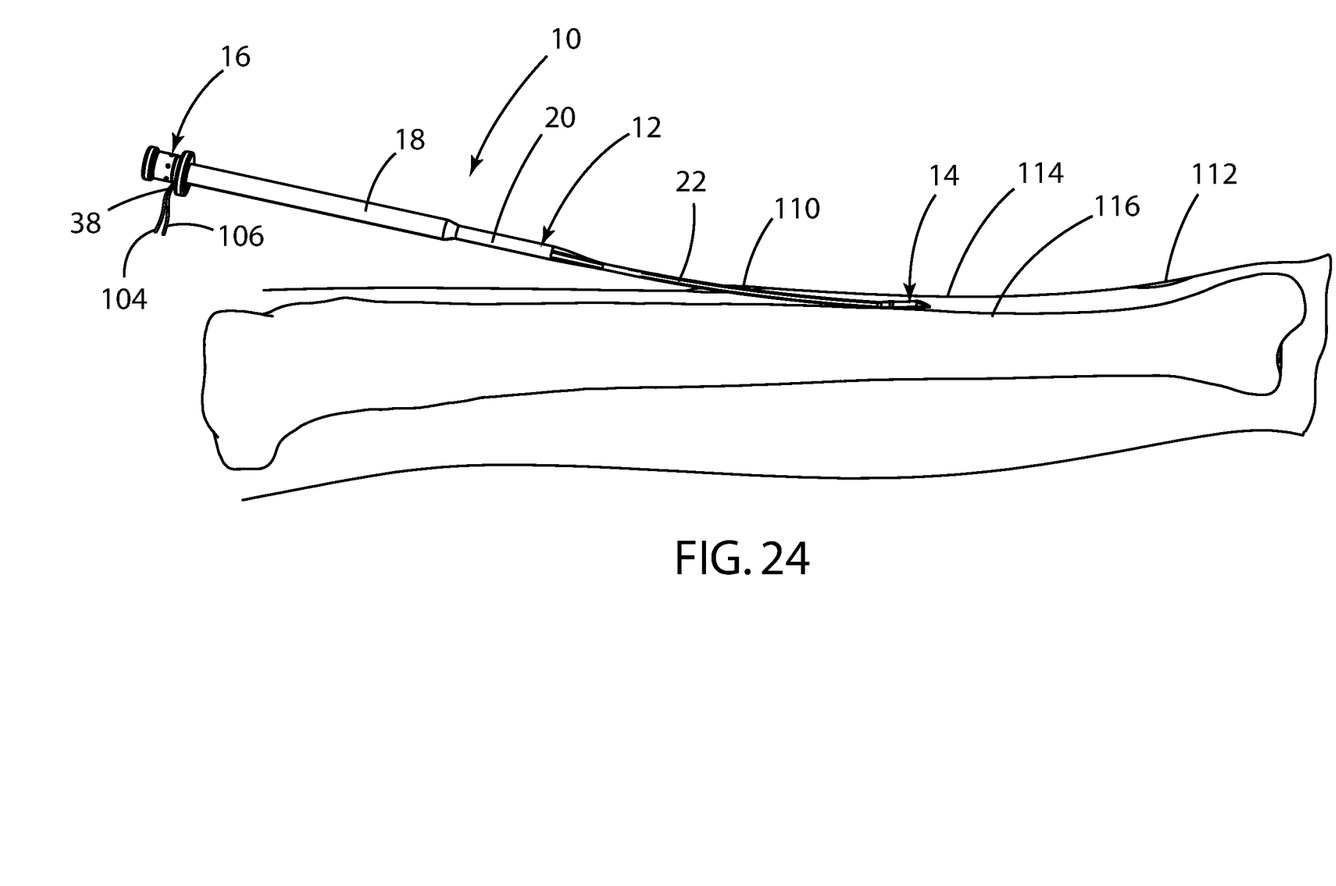
FIG. 24 is a schematic representation of a suture insertion step in a bone plate installation procedure.
Figure 25:
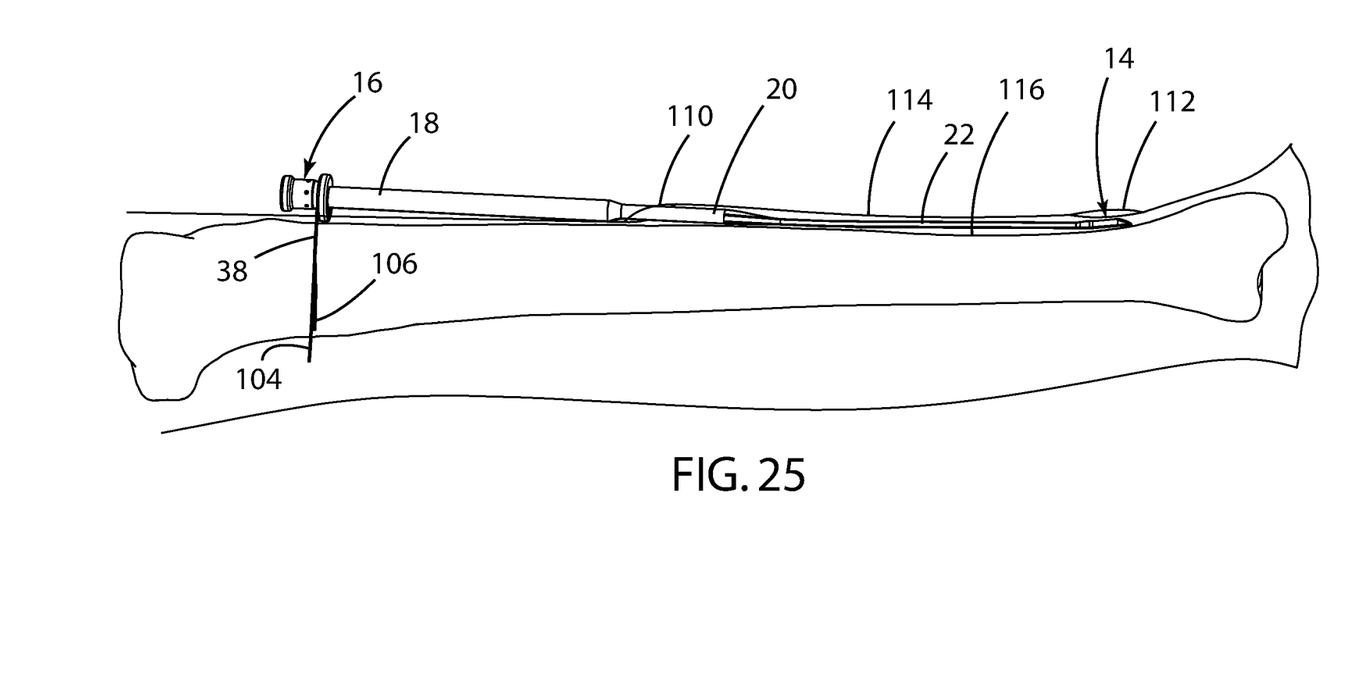
FIG. 25 is a schematic representation of a suture retrieval step in a bone plate installation.
Figure 26:
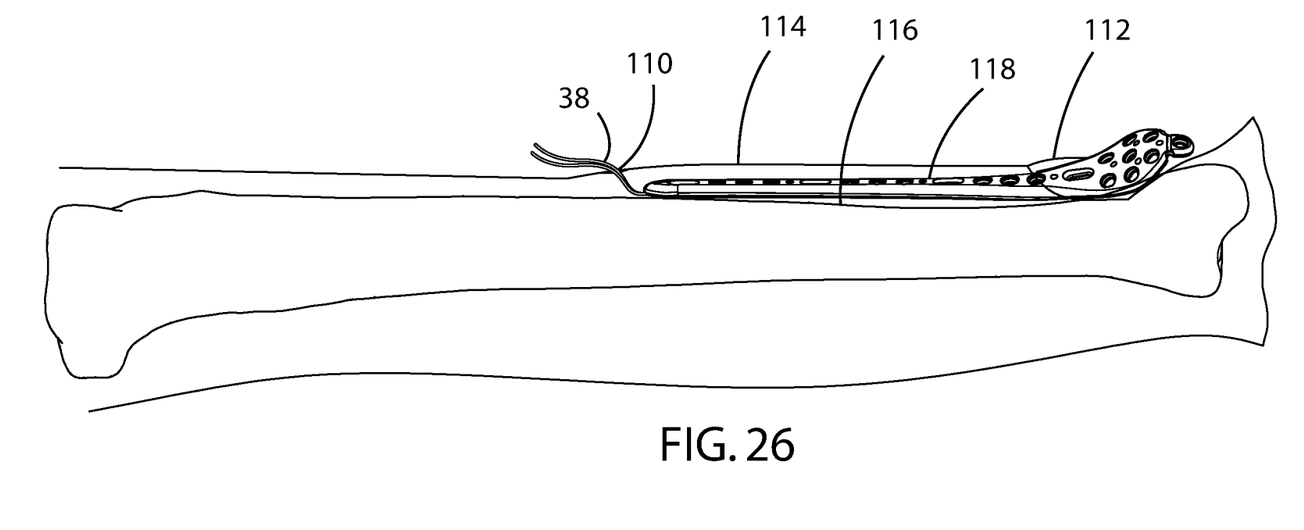
FIG. 26 is a schematic representation of a bone plate installation step using a suture in a bone plate installation.

FIGS. 24-26 illustrate a method for installing a bone plate according to one example of present invention. Initially, the loop 64 of suture or flexible member 38 is placed through the aperture 50, illustrated as the H-shaped hole, in the head 14. The loop 64 extends over the projection 52 pointing toward the tip 44. The suture or flexible member is placed in the recess 36, extending longitudinally down the underside or bottom surface 30 of the blade portion 22, and continuing in the respective transition portion 20 and handle portion 18 until reaching the retainer assembly 16.

Upon reaching the retainer assembly 16 the ends 102, 104 of the suture or flexible member 38 extend through the notch 68 in the flange 66 at the rear end of the handle portion 18.

While pulling the suture or flexible member 38 taut, knob 84 is pulled back, against the spring 100, and the ends 104, 106 of the suture or flexible member 38 are wrapped around the fastener 82 after which the knob 84 is released to secure suture or flexible member 38 in place.

Initially, as illustrated in FIG. 24, a first incision 110 and a second incision 112, spaced from the first incision 110 are made in the skin or soft tissue 114. The suture passer 10 is inserted into the first incision 110. While gripping the handle portion 18, the tip 44 and leading edge 46 of the head 14 are inserted into the first incision 110 and used to tunnel thru the first incision 110 and bluntly dissect the tissue along the bone surface 116 (periosteum) creating a passageway until the head 14 and correspondingly the suture loop 64 is visibly exposed at the second incision 112, see FIG. 25.

Using a small instrument, for example a hemostats tip, the suture loop 64 is removed from the protrusion 52. While maintaining a hold on the suture loop 64, the knob 84 is pulled rearward and the suture or flexible member ends 104, 106 are released from the retainer assembly 16. After releasing the suture or flexible member 104, 106 from the suture passer 10, the suture passer is removed.

As illustrated in FIG. 26, the suture or flexible member 38 is secured to the bone plate 118. The loose or free ends 104, 106 of the suture or flexible member 38 extending outwardly from the first incision 110 are used to pull the bone plate 118, from the first incision 110, through the second incision 112 along the passageway created by the suture passer 10 until the bone plate 118 is properly positioned. Once properly positioned, the suture or flexible member 38 is removed from the bone plate 118 and all necessary bone screws are installed.

In accordance with an example of the suture passer 10 disclosed herein, the suture passer 10 passes a suture or flexible member 38 underneath the skin and at the same time creates a passageway or tunnel through the soft tissue along the surface of the bone. The passed suture or flexible member 38 is then used to pull a bone plate 118 into position underneath the surface of the skin, avoiding the need to fully dissect open the skin in the area of the fracture.

In a further example, the projection 54 extends or points rearwardly toward the retaining assembly 16. Accordingly, the projection 54 can pull a suture or flexible member 38 rearwardly through the passageway or tunnel in the opposite direction; i.e., rather than pass the suture or flexible member from the first incision 110 to the second incision 112 wherein the suture loop 64 is removed at the second incision 112, the suture loop 64 is connected to projection 54 the suture passer 10 at the second incision 112 and is pulled toward the first incision 110 as the suture passer 10 is withdrawn or removed.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A suture passing apparatus comprising:
   an elongated body having a first end and a second end;
   a head located on said first end;
   a retainer assembly located at said second end;
   a recess in a bottom surface of said elongated body, said recess extending longitudinally from said head to said retainer assembly, a projection extending into said recess;
   said head having a top surface and a bottom surface and said recess including an aperture extending between said top surface and said bottom surface; and
   said projection extending inwardly into said aperture.

2. A suture passing apparatus comprising:
   an elongated body having a first end and a second end;
   a head located on said first end;
   a retainer assembly located at said second end;
   a recess in said elongated body, said recess extending longitudinally from said head to said retainer assembly; and
   said head having a top surface and a bottom surface and an aperture extending between said top surface and said bottom surface, said aperture having a H-shape when viewed from said top surface.

3. A suture passing apparatus comprising:
   an elongated body having a first end and a second end;
   a head located on said first end;
   a retainer assembly located at said second end;
   a recess in said elongated body, said recess extending longitudinally from said head to said retainer assembly; and
   said head includes a leading edge, said leading edge adjacent a bottom surface and a ramp surface extending from said leading edge and sloped upwards towards him a top surface of said head.

4. The apparatus of claim 3 wherein said leading edge has an arcuate configuration swept rearwardly toward said elongated body; and
   said bottom surface of said head is a substantially planar surface.

5. The apparatus of claim 3 wherein a portion of the elongated body has a substantially rectangular cross-sectional shape wherein upper and lower sides defined by the top and bottom surface are greater in length than the opposing sides defined by the respective side surfaces.

6. The apparatus of claim 3 wherein said elongated body has a bending axis perpendicular to the longitudinal axis of the elongated body and parallel to a lateral axis extending between the respective side surfaces.

7. The apparatus of claim 3 wherein said retainer assembly includes a hub, said hub movably secured to said elongated body.

8. The apparatus of claim 3 wherein said elongated body includes a shank portion and a handle portion.

9. An instrument for passing a suture comprising:
   an elongated body having a first end and a second end;
   a head located on said first end, said head having a top surface, a bottom surface and a tip, an aperture having a continuous perimeter extends between said top surface and said bottom surface;
a projection extending into said aperture, said projection not extending above the top surface of said head adjacent said continuous perimeter of said aperture; and
said elongated body having a recess extending longitudinally from said projection to said second end.

10. An instrument as set forth in claim 9 including
a retainer assembly located at said second end; and
said recess extending longitudinally from said projection to said retainer assembly.

11. An instrument as set forth in claim 9 including said aperture having an H-shape when viewed from said top surface.

12. An instrument as set forth in claim 9 including said elongated body having a shank portion and a handle portion, said shank portion having a substantially rectangular cross-sectional shape.

13. An instrument as set forth in claim 9 wherein said elongated body has a bending axis perpendicular to the longitudinal axis of the elongated body and parallel to a lateral axis of the elongated body.

14. A method of installing a bone plate comprising the steps of:
providing an instrument having an elongated body including a head portion including an aperture and a post member extending into said aperture and a recess extending from said aperture along said elongated body;
placing a loop of a flexible member in the aperture and over the post, placing the flexible member in the recess extending from said aperture along said elongated body;
using the instrument, specifically the head portion to create a passageway adjacent underlying bone;
removing the loop of flexible member from the post;
securing the flexible member to a bone plate;
removing the instrument; and
using the flexible member to pull the bone plate through the passageway and into position.

15. The method set forth in claim 14 wherein the head portion includes a leading edge and a rearwardly sloped surface that reflects the attached periosteum from the underlying bone.

16. The method set forth in claim 14 including the step of pulling the flexible member taut and using a retainer assembly to secure the free ends of the flexible member to the instrument.

17. The method set forth in claim 14 including the step of removing the flexible member from the bone plate and installing bone screws to secure the bone plate to the bone.

18. The method set forth in claim 14 wherein the head portion includes a leading edge and a rearwardly sloped surface that reflects the attached periosteum from the underlying bone.

19. A method of installing a bone plate comprising the steps of:
providing an instrument having an elongated body including a head portion including an aperture and a post member extending into said aperture and a recess extending from said aperture along said elongated body;
using the instrument, specifically the head portion to create a passageway adjacent underlying bone;
securing a flexible member to a bone plate;
attaching said flexible member to said instrument and removing the instrument thereby pulling the flexible member through the passageway; and
using the flexible member to pull the bone plate through the passageway and into position.

* * * * *